United States Patent [19]
> Patience

[11] 4,361,231
[45] Nov. 30, 1982

[54] SPONGE COLLECTION DEVICE
[75] Inventor: Donald Patience, Cary, Ill.
[73] Assignee: The Kendall Company, Boston, Mass.
[21] Appl. No.: 245,008
[22] Filed: Mar. 18, 1981
[51] Int. Cl.³ .................... B65D 30/22; B65D 33/02; B65D 33/14; B65D 85/00
[52] U.S. Cl. ........................................ 206/362; 150/1; 206/286; 206/554; 206/806; 229/56
[58] Field of Search ............ 206/438, 362, 806, 526, 206/554, 286, 390; 229/62, 69, 56; 150/1

[56] References Cited
U.S. PATENT DOCUMENTS 4,176,746 12/1979 Kool ................................ 206/438
4,234,086 11/1980 Dorton ........................... 206/362

*Primary Examiner*—William T. Dixson, Jr.
*Attorney, Agent, or Firm*—Powell L. Sprunger

[57] ABSTRACT

A sponge collection device comprising, a backing sheet of flexible material having a front surface, a rear surface, a pair of side edges, and a pair of end edges connecting the side edges. The device has a plurality of pockets progressively disposed on the front surface of the backing sheet intermediate the end edges. The pockets comprise a flap of flexible material having a pair of side edges, and an upper edge extending between the side edges, with side portions of the flap adjacent its side edges being joined to the backing sheet adjacent the side edges of the backing sheet. The upper edge of the flap defines an opening intermediate the flap and backing sheet to receive sponges, with a lower portion of the flap being joined to the backing sheet along a line intermediate the side portions of the flap. The joinder line extends upwardly from each of the flap side portions toward a raised central portion of the joinder line.

6 Claims, 3 Drawing Figures

SPONGE COLLECTION DEVICE

BACKGROUND OF THE INVENTION

The present invention relates to collection devices for surgical sponges.

During surgical procedures, absorbent sponges are utilized to absorb body fluids around the site of the surgical incision. The sponges are normally provided in two sizes, a 4-inch by 4-inch smaller sponge, and a 14-inch by 14-inch larger laparotomy sponge. In the past, when the wetted sponges were removed from the patient's body, they have been placed in a kick bucket for retention during the surgical procedure. At the end of the surgical procedure, the sponges were removed from the kick bucket, and were sorted according to size, after which they were counted to assure that no sponges were left in the patient's body. According to convention, the 4-inch by 4-inch sponges were counted in groups of ten, and the 14-inch by 14-inch sponges were counted in groups of five.

It will be apparent that the prior sorting and counting procedure was tedious and time consuming, and could be subject to error during the counting of sponges. A bag strip has been proposed in U.S. Pat. No. 3,749,237 in an attempt to facilitate this procedure.

SUMMARY OF THE INVENTION

A principal feature of the present invention is the provision of an improved sponge collection device of simplified construction.

The sponge collection device comprises, a backing sheet of flexible material having a front surface, a rear surface, a pair of side edges, and a pair of end edges connecting the side edges. The device has a plurality of pockets progressively disposed on the front surface of the backing sheet intermediate the end edges. The pockets comprise a flap of flexible material having a pair of side edges, and an upper edge extending between the side edges, with side portions of the flap adjacent its side edges being joined to the backing sheet adjacent the side edges of the backing sheet. The upper edge of the flap defines an opening intermediate the flap and backing sheet to receive sponges. The device has a lower portion of the flap being joined to the backing sheet along a line intermediate the side portions of the flap, with the joinder line extending upwardly from each of the flap side portions toward a raised central portion of the joinder line.

A feature of the present invention is that a pair of smaller sponges may be placed in the pocket on opposed sides of the pocket.

Another feature of the invention is that one larger sponge may be placed in each pocket, or a pair of larger sponges may be placed on opposed sides of the pocket.

Thus, a feature of the present invention is that the device collects either smaller or larger sponges in the pockets.

Still another feature of the invention is that the device facilitates retention of the soiled sponges during a surgical procedure.

Yet another feature of the invention is that the device facilitates counting of the sponges after the surgical procedure has been completed.

Further features will become more fully apparent in the following description of the embodiments of this invention and from the appended claims.

DESCRIPTION OF THE DRAWINGS

In the drwings.

DESCRIPTION OF THE PREFERRED EMBODIMENTS

Figure 1:
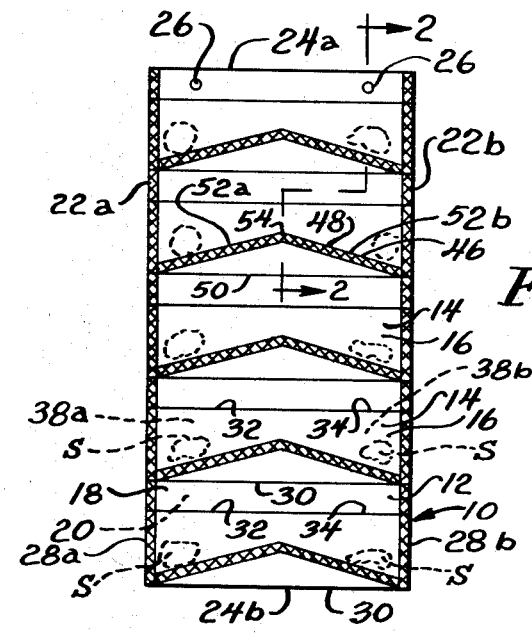
FIG. 1 is a front plan view of the sponge collection device of the present invention showing the device as used for collecting smaller sponges.
Figure 2:
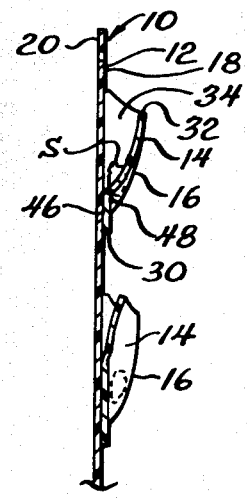
FIG. 2 is a fragmentary sectional view taken substantially as indicated along the line 2—2 of FIG. 1.

Referring now to FIGS. 1 and 2, there is shown a sponge collection device generally designated 10 comprising a backing sheet 12 of flexible material and a plurality of pockets 14 each comprising a flap 16 of flexible material joined to the backing sheet 12. The backing sheet 12 and flaps 16 may be constructed from any suitable plastic material, such as polyethylene. The backing sheet 12 has a generally rectangular shape, and has a front surface 18, a rear surface 20, a pair of opposed side edges 22a and 22b, and a pair of opposed end edges 24a and 24b connecting the side edges 22a and b. The backing sheet 12 may have a pair of spaced openings 26 located adjacent the end edge 24a for suspending the device 10 from a suitable instrument received through the openings 26.

The flaps 16 have a pair of opposed side edges 28a and 28b, a lower edge 30 extending between the side edges 28a and b, and an upper edge 32 extending between the side edges 28a and b. As shown, the side edges 28a and b of the flaps 16 are joined to the front surface 18 of the backing sheet 12 adjacent the side edges 22a and b of the backing sheet 12 by suitable means, such as by heat sealing. The upper edges 32 of the flaps 16 define associated openings 34 intermediate the flaps 16 and backing sheet 12 to receive soiled sponges in the pockets 14. Also, the pockets 14 are progressively disposed along the backing sheet 12 between the end edges 24a and b, with the upper edges 32 of loer flaps 16 being located adjacent the lower edges 30 of adjacent upper flaps 16. In a preferred form, the device 10 has five pockets 14 disposed along the backing sheet 12 for a purpose which will be described below.

Figure 3:
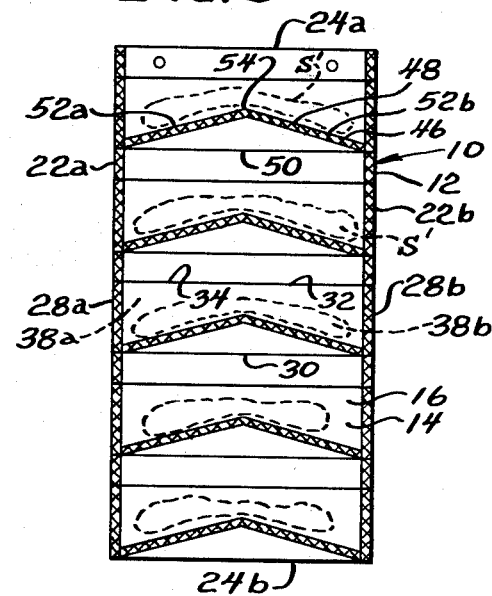
FIG. 3 is a front plan view of the sponge collection device showing the device as used for collecting larger sponges.

As shown, lower portions 46 of the flaps 16 are joined to the backing sheet 12 along a line 48 extending between lower parts of the side edges 28a and b of the flaps 16. The joinder line 48 extends upwardly from each of the flap side edges 28a and b toward a raised central portion of the joinder line 48. In a preferred form, the joinder lines 48 define the shape of a triangle, with the base 50 of the triangles extending along the lower edges 30 of the flaps 16 between the junctures of the joinder lines 48 and the side edges 28a and b of the flaps 16. Two sides 52a and 52b of the triangles extend from the side edges 28a and b toward an apex 54 of the triangles located generally centrally between the side edges 28a and b of the flaps 16, with the sides 52a and b being approximately of equal length. The joinder lines 48 separate each pocket 14 into a pair of compartments 38a and b to receive a pair of smaller sponges at locations in the compartments 38a and b adjacent the juncture of the joinder lines 48 and the flap side edges 28a and b. Alternatively, as shown in FIG. 3, one larger sponge may be placed in each of the pockets 14, with each larger sponge extending over the apex 54 and along the sides 52a and b of the triangles, or a pair of larger sponges may be placed on opposed sides of the pockets in a manner similar to the smaller sponges.

In use, with reference to FIGS. 1 and 2, the backing sheet 12 is suspended by a suitable instrument passing through the openings 26 of the backing sheet 12. During a surgical procedure, smaller soiled sponges S may be placed in the pockets 14, with each smaller sponge S being located in one of the compartments 38a and b. Thus, during collection of smaller sponges S by the device 10, two smaller sponges S are placed in each pocket 14 on opposed sides of the flap 16. Since five pockets 14 are located on each backing sheet 12, a total of ten smaller sponges S may be collected in each of the devices 10 during the placement procedure. Thus, the device 10 serves to collect the soiled sponges S in the pockets 14, and automatically counts a total of ten smaller sponges S in each of the devices 10. Howver, with reference to FIG. 3, when larger soiled sponges S' are removed from the patient's body, one larger sponge S' may be placed in each of the pockets 14, with opposed ends of the larger sponges S' being located in the opposed compartments 38A and b of each pocket 14. Thus, the device 10 may also be utilized to collect larger sponges S', and since there are five pockets 14 located in each device 10, the device 10 collects and automatically counts five larger sponges S' in the pockets 14 of each device 10. Accordingly, the joinder line 48 divides the pockets 14 into the compartments 38a and b to permit selective placement of two smaller sponges S in each compartment 38a and b, or a larger sponge S' in each pocket 14. Thus, the soiled sponges may be separated into smaller and larger sponges during the collection and counting procedure in each of the devices 10.

The foregoing detailed description is given for clearness of understanding only, and no unnecessary limitations should be understood therefrom, as modifications will be obvious to those skilled in the art.

I claim:

1. A sponge collection device, comprising:
   a backing sheet of flexible material having a front surface, a rear surface, a pair of side edges, and a pair of end edges connecting the side edges; and
   a plurality of pockets progressively disposed on the front surface of the backing sheet intermediate said end edges, said pockets comprising a flap of flexible material having a pair of side edges, and an upper edge extending between said side edges, with side portions of the flap adjacent its side edges being joined to the backing sheet adjacent the side edges of the backing sheet, with the upper edge of the flap defining an opening intermediate the flap and backing sheet to receive sponges, and with a lower portion of the flap being joined to the backing sheet along a line intermediate the side portions of the flap, said joinder line extending upwardly from each of the flap side portions toward a raised central portion of the joinder line.

2. The device of claim 1 wherein the joinder line defines the shape of a triangle with the base of the triangle extending between the juncture of the joinder line and the flap side portions, with two sides of the triangle extending along the joinder line, and with the apex of the triangle being located in the region of said central portion of the joinder line.

3. The device of claim 1 wherein the backing sheet is generally rectangular.

4. The device of claim 1 wherein the side portions of the flap comprise the side edges of the flap.

5. The device of claim 1 wherein the device has five flaps located progressively along the backing sheet.

6. The device of claim 1 including a pair of spaced openings adjacent an upper edge of the backing sheet.

* * * * *